(12) United States Patent
Suon et al.

(10) Patent No.: US 9,463,059 B2
(45) Date of Patent: Oct. 11, 2016

(54) CUTTING TOOL WITH CIRCULATING WIRE

(71) Applicants: Naroun Suon, Lawrence, MA (US); Ra Nam, Lawrence, MA (US); Samuel Raybin, Marlborough, MA (US); Paul Smith, Smithfield, RI (US); Jonathan Root, Groveland, MA (US)

(72) Inventors: Naroun Suon, Lawrence, MA (US); Ra Nam, Lawrence, MA (US); Samuel Raybin, Marlborough, MA (US); Paul Smith, Smithfield, RI (US); Jonathan Root, Groveland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 284 days.

(21) Appl. No.: 13/763,220

(22) Filed: Feb. 8, 2013

(65) Prior Publication Data
US 2013/0211403 A1 Aug. 15, 2013

Related U.S. Application Data

(60) Provisional application No. 61/596,925, filed on Feb. 9, 2012.

(51) Int. Cl.
| | |
|---|---|
| A61B 17/26 | (2006.01) |
| A61B 18/14 | (2006.01) |
| A61B 18/04 | (2006.01) |
| A61B 17/32 | (2006.01) |
| A61B 18/00 | (2006.01) |
| A61B 17/00 | (2006.01) |

(52) U.S. Cl.
CPC .............. *A61B 18/04* (2013.01); *A61B 17/32* (2013.01); *A61B 18/149* (2013.01); *A61B 18/1485* (2013.01); *A61B 18/1492* (2013.01); *A61B 2017/00269* (2013.01); *A61B 2018/00184* (2013.01); *A61B 2018/141* (2013.01); *A61B 2018/144* (2013.01); *A61B 2018/1407* (2013.01); *A61B 2018/1475* (2013.01)

(58) Field of Classification Search
USPC .................................................. 606/170, 113
See application file for complete search history.

(56) References Cited

U.S. PATENT DOCUMENTS

| | | |
|---|---|---|
| 2002/0095168 A1 | 7/2002 | Griego et al. |
| 2003/0060842 A1 | 3/2003 | Chin et al. |
| 2006/0064113 A1 | 3/2006 | Nakao |
| 2010/0057077 A1 | 3/2010 | Ducharme |

FOREIGN PATENT DOCUMENTS

| | | |
|---|---|---|
| DE | 20 2007 006 619 U1 | 8/2007 |
| WO | WO 2004/073524 A1 | 9/2004 |

*Primary Examiner* — Carl H Layno
*Assistant Examiner* — Jon Eric C Morales
(74) *Attorney, Agent, or Firm* — Bookoff McAndrews, PLLC

(57) ABSTRACT

A medical device and related method of use for cutting tissue is described. The device includes an elongate tubular member having a proximal end, a distal end, and first and second lumens extending between the proximal and distal ends. The device further includes a first elongate arm having a third lumen extending distally from the first lumen and a second elongate arm having a fourth lumen extending distally from the second lumen. A cutting element extends from the third lumen of the first arm to the fourth lumen of the second arm, such that the cutting element is slidably disposed in at least one of the third and fourth lumens.

20 Claims, 9 Drawing Sheets

FIG. 4A     FIG. 4B

ND WIRE

This application claims the benefit of U.S. Provisional Application No. 61/596,925, filed Feb. 9, 2012, the disclosure of which is incorporated herein in its entirety.

DESCRIPTION OF THE INVENTION

1. Field of the Invention

This disclosure generally relates to dissection of bodily tissue. Specifically, this disclosure includes apparatus for performing electrosurgery, electrocauterization, and electrocoagulation of tissue working in conjunction with an endoscope.

2. Background of the Invention

Organ walls are composed of several layers, which may include the mucosa (the surface layer), the submucosa, the muscularis (muscle layer), and the serosa (connective tissue layer). In gastrointestinal, colonic, and esophageal cancer, e.g., small polyps or cancerous masses may form along the mucosa and often extend into the lumens of the organs. Conventionally, that condition is treated by cutting out a portion of the affected organ wall. This procedure, however, may be difficult to perform, and may cause discomfort to patients, and pose health risks. Recently, physicians have adopted a minimally invasive technique called endoscopic mucosal resection (EMR), and another called endoscopic submucosal dissection (ESD), which removes the cancerous or abnormal tissues (e.g., polyps), keeping the walls intact.

EMR is generally performed with an endoscope, which is a long, narrow elongated guide member optionally equipped with a light, video camera, and other instruments. Those of ordinary skill will recognize that the term "endoscope" as used herein is merely for exemplary purposes, and that any suitable introduction sheath may be used with the principles of the present disclosure. During EMR, the endoscope may be passed down the throat or guided through the rectum to reach an abnormality such as a polyp in an affected organ. The distal end of the endoscope, for example, further equipped with a cap carrying a small wire loop or a band, is guided towards the polyp or any other undesired tissue. Once there, suction may be applied through a lumen in the endoscope, or some other retraction tool extending from the endoscope is retracted, to draw the undesired tissue towards the endoscope cap. When the undesired tissue is sufficiently drawn into the cap, the wire loop or band can be closed around the undesired tissue, resecting it from the organ wall, or banding it. Subsequently, the excised tissue may be extracted by e.g., the vacuum, for examination, biopsy, or disposal.

Certain polyps, such as pedunculated polyps, are characterized by a stalk attached to the mucosal layer. Drawing such polyps into the cap, without drawing in any other tissue, is readily possible. Certain other polyps, such as sessile polyps, however, exhibit a broad base, and lay flat on the mucosal surface and are often devoid of a stalk. It may be difficult to grasp these polyps, without drawing in a part of the muscularis layer. Conventional EMR caps include axial channels for introducing devices or instruments proximate the affected area. Because polyps or lesions are present on the organ walls, it is often difficult to grasp such objects readily with axially extending devices.

Therefore, there exists a need for an improved endoscopic mucosal resection tool that aids in grasping and/or resecting both pedunculated and sessile polyps without damaging the surrounding tissue or muscle layers of the organ.

SUMMARY OF THE INVENTION

Embodiments of the present disclosure relate to a medical device for resecting an undesired mass from a patient's body using a minimally invasive surgical method and tool.

In accordance with an aspect of the present disclosure, a medical device may include an elongate tubular member including a proximal end, a distal end, and first and second lumens extending between the proximal and distal ends. A first elongate arm may include a third lumen and may extend distally from the first lumen. A second elongate arm may include a fourth lumen and may extend distally from the second lumen. A cutting element may extend from the third lumen of the first arm to the fourth lumen of the second arm, and may be slidably disposed in at least one of the third and fourth lumens.

In various embodiments, the device may include one or more of the following features: the device may further comprise an introduction sheath; the cutting element may extend from the proximal end of the tubular member to the distal end; the cutting element may be a cautery wire; a mechanism for moving the cutting wire relative to at least one of the lumens of the first and second arms; the mechanism may be configured to move the cutting wire such that a portion disposed between the first and second elongate arms may be advanced into one of the first and second arms; the mechanism may include a pulley; the mechanism may be configured to be coupled to an energy source; the energy source may be an electrical energy source; the first and second arms may be configured to transition between collapsed and expanded configurations; the arms may be movable relative to the elongate member; the elongate tubular member may extend in a first plane and the ends of the arms may be disposed in a second plane spaced from the first plane; and at least one of the first and second elongate arms may be configured to transition from a collapsed configuration to an expanded configuration.

In accordance with another aspect of the invention, an medical device may include an elongate tubular member including a proximal end and a distal end. A plurality of flexible arms extends distally from the distal end, wherein each of the flexible arms defines a lumen therethrough, and wherein each of the plurality of flexible arms is configured to transition between a first configuration and a second configuration. The medical device may further include a cutting wire extending from one of the plurality of flexible arms to another of the plurality of flexible arms, and the cutting wire may be slidably disposed within the lumen of at least one of the flexible arms.

In various embodiments, the medical device may include one or more of the following features: the cutting wire may be a cautery wire; the first configuration may be a collapsed configuration and the second configuration may be an expanded configuration; a mechanism for sliding the cutting wire relative to the at least one of the flexible arms; a portion of the arms may include radiopaque markers; and the wire may include one of protrusions, indentations, and serrations; the wire may include a blade edge.

In accordance with an alternate aspect of the disclosure, a method for tissue manipulation may include inserting a medical device within a body lumen. The medical device may include an elongate tubular member including a proximal end, a distal end, and first and second lumens extending between the proximal and distal ends. A first elongate arm may include a third lumen and may extend distally from the first lumen. A second elongate arm may include a fourth lumen and may extend distally from the second lumen. A cutting element may extend from the third lumen of the first arm to the fourth lumen of the second arm and may be slidably disposed in at least one of the third and fourth lumens. The method may further include advancing the elongate member towards target tissue such that a portion of the cutting element contacts the target tissue; resecting the target tissue; and moving the portion of the cutting element into one of the third and fourth lumens so that a second portion of the cutting element is in position for tissue contact.

In various embodiments, the first and second arms may be configured to transition between a collapsed configuration and an expanded configuration.

Additional objects and advantages of the claimed disclosure will be set forth in part in the description which follows, and in part will be obvious from the description, or may be learned by practice of the disclosure. The objects and advantages of the disclosure will be realized and attained by means of the elements and combinations particularly pointed out in the appended claims.

It is to be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate embodiments of the present disclosure and together with the description, serve to explain the principles of the embodiments disclosed herein.

DESCRIPTION OF THE EMBODIMENTS

Figure 1:
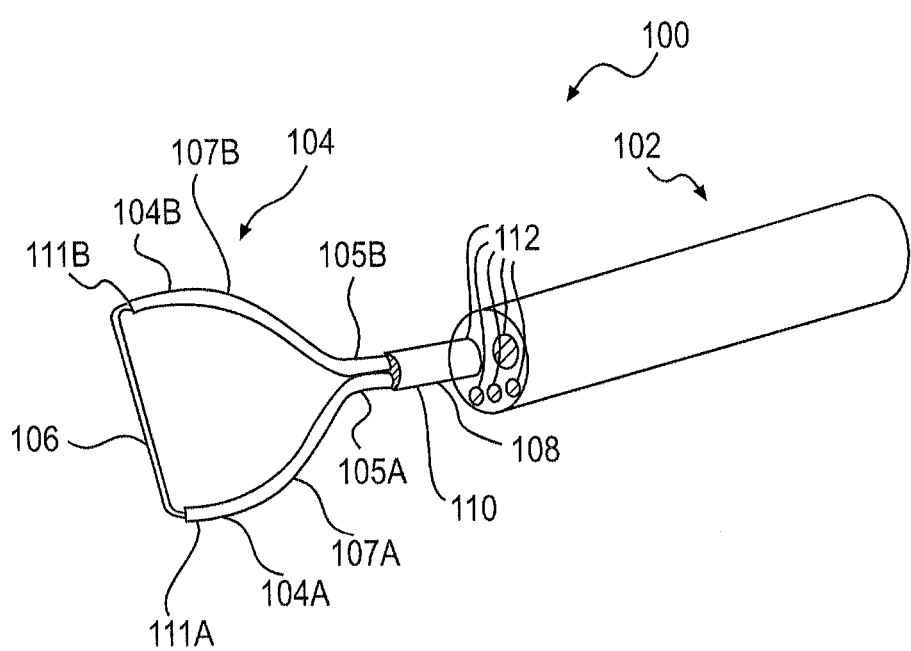
FIG. 1 is a perspective view of a cutting tool, according to an embodiment of the present disclosure.

Reference will now be made in detail to embodiments of the present disclosure, examples of which are illustrated in the accompanying drawings. Wherever possible, the same reference numbers will be used throughout the drawings to refer to the same or like parts.

Overview

The present disclosure addresses a device for improving tissue dissection methods for, among other things, endoscopic submucosal dissection (ESD) or endoscopic mucosal resection (EMR). The device may include a Y-shaped structure including a shaft and two arms extending outwards from a distal end of the shaft, which may be preformed to define a Y-shape. For example, the arms may be disposed at any suitable angle at any point along their length, but especially at the distal portions of the arms. A wire may be run through the shaft, up to the distal end of one of the pre-formed arms, across the gap between the distal ends of two arms and back down the other arm into the shaft. In some embodiments, the wire may be adapted for electrocautery resection, and the arms are mounted to prevent electrical contact between them. In non-cautery embodiments, the wire may be configured to cut through tissue. A wire moving mechanism, for example, a pulley located at the proximal portion of the endoscope may be included to withdraw a used portion of the wire back into the shaft, exposing additional wire cutting surface. In some embodiments, the movement of the wire could aid tissue resection.

As the term ESD suggests, embodiments of the present disclosure are often employed with endoscopes. The term "endoscope" is used herein to refer to any of the family of devices having an elongate member capable of carrying any of a number of medical devices to a location within a patient's body for surgery, treatment, or diagnosis. Examples of such devices are colonoscopes, upper endoscopes, bronchoscopes, thoracoscopes, laparoscopes, ureteroscopes, cholangioscopes, duodenoscopes, hysteroscopes or similar devices now known or hereafter developed. Such devices may also include any suitable introduction sheath or similar devices. Also, as used herein, the term "distal" refers to the end of a device, or the direction, farthest away from the device operator, while "proximal" refers to the end closest to the operator.

Embodiments of the present disclosure can be used in a variety of diagnostic or therapeutic procedures, including resection of lesions, tumors, or otherwise undesired tissue, or for tissue collection for biopsy during procedures such as colonoscopy, upper endoscopy, or bronchoscopy. Although exemplary embodiments of the present disclosure are described with reference to endoscopes, it will be appreciated that aspects of the present disclosure may have wide application. Thus, the resection device of the present disclosure may be suitable for use with other medical devices, where tissue resection or dissection is desirable. Accordingly, the following descriptions and illustrations should be considered illustrative in nature, not limiting the scope of the claimed disclosure.

Exemplary Embodiments

FIG. 1 provides a perspective view of one embodiment of a resection system 100. The system 100 may be disposed through a minimally invasive surgical system, such as an endoscope or guide device 102, for performing intraluminal and/or transluminal surgery through an incision or a natural body opening. The system 100 includes a frame 104, including a plurality of arms 104A, 104B, extending from a distal end 110 of a catheter 108. Although the depicted embodiments illustrate two arms 104A, 104B, those of ordinary skill in the art will recognize that any suitable number of arms may be provided.

Arms 104A, 104B include relatively straight base portions 105A, 105B and predefined angular portions 107A, 107B that may diverge at angles to form the shaped frame, such as a Y-shaped frame 104. As depicted, portions 107A, 107B may diverge from the portions 105A and 105B at similar angles. In some embodiments, portions 107A, 107B may diverge at different angles to form an asymmetrical Y-shaped frame 104. As shown, each arm 104A, 104B may be formed of multiple bends. In some embodiments, distal end portions 111A, 111B may lie in a plane approximately perpendicular to the remainder of the frame 104. In general, distal ends 111A, 111B are bent at an angle to the rest of the portions 107A, 107B and 105A, 105B. It should be understood that angle and direction of each bend may be varied selectively based on the intended use and application. For example, if the target tissue is small, the distal ends of the arms 104A, 104B may be partially extended out of the catheter 108, such that divergence angle α is acute. Alternatively, the arms may form an obtuse angle α if the target area is large. Super elastic materials such as nitinol, stainless steel, cobalt chromium, tantalum noted above, are well-suited to this requirement. Super elastic materials are available to the art in both solid and braided forms, as may be desired for particular applications.

In addition, each of arms 104A, 104B may include hollow structure allowing passage for a wire or similar cutting device. A wire 106, which may serve has a cutting tool, having its two ends passing through the distal openings of the arms 104A and 104B, and extending along the length of the arms up to the endoscope 102. Alternatively, the wire may be an electrocautery wire or may conduct energy.

The resection system 100 may be disposed within an endoscope 102. As can be seen, and is generally known in the art, endoscopes often include a number of working channels 112. Here, the catheter 108 may be disposed in a working channel 112 such that the frame 104 remains outside the channel 112. The following paragraphs describe the various components of the system 100 in detail.

In some embodiments, the frame 104 may be expandable. The frame may be disposed within catheter 108, which is further disposed within channel 112. When appropriately positioned, catheter 108 may be advanced distally out of channel 112 and frame 104 may be advanced out of a lumen of catheter 108 to expand into a preformed shape. Frame 104 may expand using known expansion mechanisms. Frame 104 may be made of a elastic material, such as Nitinol, or the frame 104 may expand by actuating a expansion mechanism. Suitable expansion mechanism may include, for example, springs, inflation balloon, pull strings, etc.

One can readily observe that the specific shape of the frame 104 determines the distance, direction, and character of the spacing between the distal tip of the catheter 108 and the cutting wire 106. The effective length of cutting wire 106 can be relatively long or short, depending on the angles formed by angular portions 104A, 104B. The system 100 can perform operations spaced more or less laterally from the axis of the endoscope, depending on the length and angle of tip portions 111A, 111B; and the effective operating distance from the distal tip of catheter 108 depends on the length of the overall frame 104. These and other choices can be exercised by those in the art to tailor the disclosed medical device to particular anatomy environments, tasks, and scenarios.

Figure 1A:
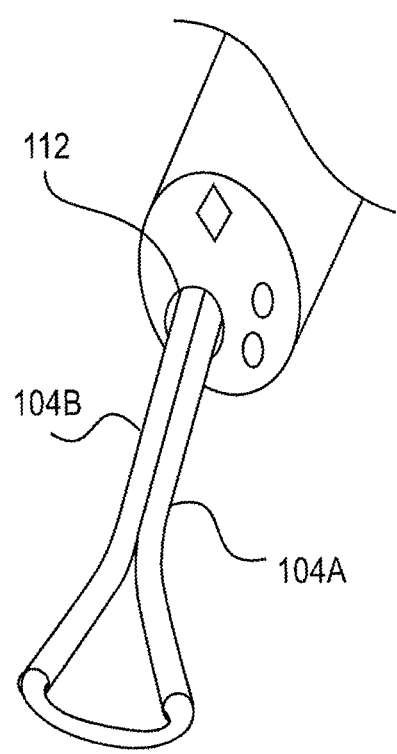
FIG. 1A is a perspective view of a cutting tool, according to an embodiment of the present disclosure.

In some embodiments, arms 104A, 104B may extend from a distal end of the endoscope or guide device 102 without catheter 108. For example, as shown in FIG. 1A, the arms 104A, 104B may extend from a single channel 112, or from separate channels 112. In these embodiments and others, the arms 104A, 104B may be separate elements extending through the channel or channels so that they are independently actuatable and longitudinally movable relative to one another. In such embodiments, arms 104A, 104B may or may not contact each another. Alternatively, arms 104A, 104B may be connected to each other along all or some portion proximal to the predefined angular portions 107A, 107B, or may merge, for instance to a single lumen, at a position proximal to the distal end of the endoscope or guide device 102. In such embodiments, arms 104A, 104B may be coextruded together and may move longitudinally as one piece.

Figure 2:
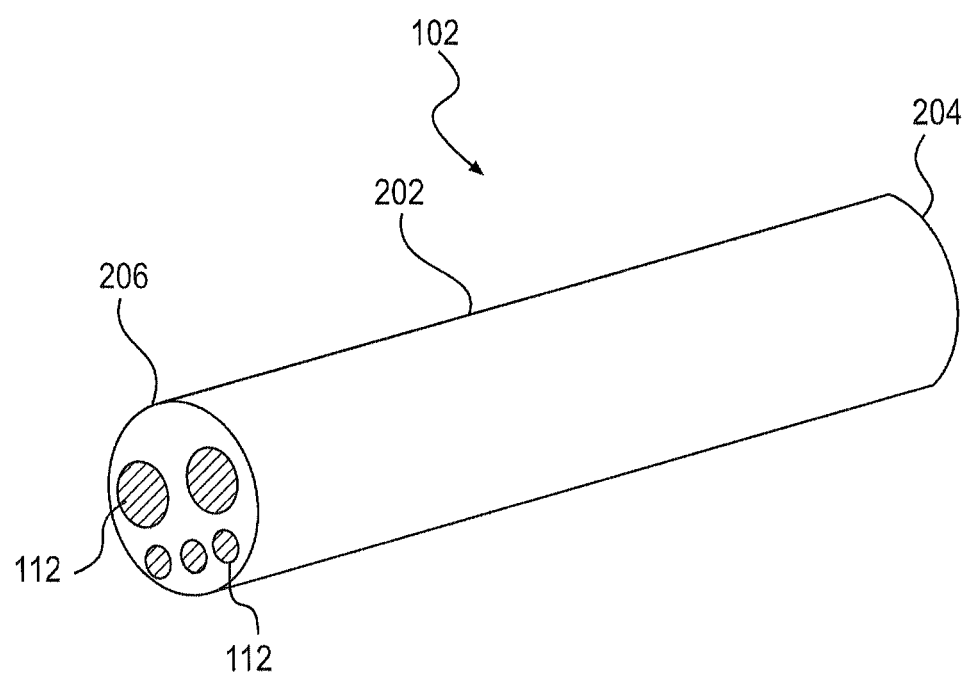
FIG. 2 is a perspective view of a proximal portion of an introduction sheath for use with the tool of FIG. 1.

FIG. 2 provides a perspective view of the distal portion of endoscope 102. Distal end 206 of elongate member 202 may have a swivel motion, which allows the distal end 206 to be steerable in all directions. Further, the distal end 206 may be rotatable about a longitudinal axis. Also, channels 112 may be used for irrigation, suction, or insufflations. Distal end 206 may have retaining members (not shown) such as expandable members (e.g., balloons), tines, or barbs for holding distal end in a desired position. In some embodiments, the retaining members may be selectively activated.

The outer surface of elongate member 202 may include any suitable coating and/or covering. For example, an outer surface of elongate member 202 may include a layer of lubricous material to facilitate insertion of elongate member 202 through a body lumen or surgical insertion. As noted above, elongate member 202 may define one or more channels 112 adapted to guide at least one elongate tool or viewing device, or the like, to a surgical site. The surfaces of the channels within elongate member 202 may also include any suitable coating or covering. In addition, a portion of the channels within elongate member 202 may include one or more suitable sealing mechanisms (not shown), to inhibit or prevent the flow of bodily fluids and/or materials through the elongate member 202. Likewise, the sealing mechanisms may help prevent the insertion of unwanted materials through elongate member 202. In one embodiment, a suitable sealing mechanism may include an elastomeric barrier having an expandable opening.

As also shown in FIG. 2, elongate member 202 may include one or more channels 112. The channels may be sized and configured to accommodate any suitable tool or combination or suite of tools. For example, relatively large channels could be provided for instruments such as forceps or a snare device, with relatively smaller channels provided to accommodate an illumination device and a camera. Those in the art are aware of the various possibilities in this regard. In addition, elongate member 202 may be prefabricated with components such as those suitable for illumination and/or imaging within a patient's body.

Figure 3:
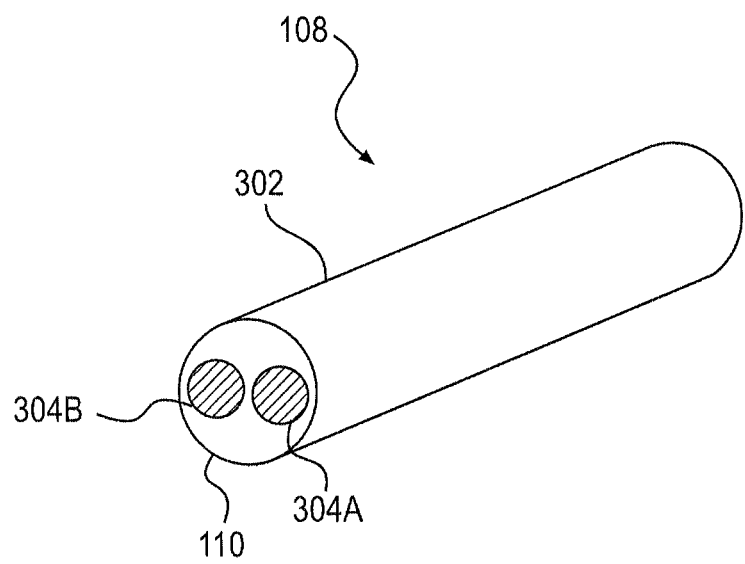
FIG. 3 is a perspective view of a sheath of the tool shown in FIG. 1.

In the embodiment shown in FIG. 1, elongate member 202 accommodates a catheter 108 extending through a channel 112. An embodiment of catheter 108 is depicted in FIG. 3. Catheters are formed in a number of configurations designed to accomplish particular tasks, and the catheter 108 is particularly adapted to carry the cutting tool disclosed here. In particular, since the disclosed cutting tool may conduct electricity, the catheter may be configured to provide separately formed lumens to ensure that no electrical short-circuit is formed. Moreover, the catheter material may be an insulator, protecting the endoscope from any current leakage. Typical catheter materials include, but are not limited to polymers, such as polyethylene or nylon. In some embodiments, the catheter 108 as a whole may be formed as an elongated tube 302, having one or more lumens, such as, e.g., two lumens 304A, 304B extending from end to end. The catheter 108 may be formed from flexible material, adapted for easy navigation through bodily passages. Catheter 108 may further comprise reinforcement such as braiding or coiling along any portion. Catheter 108 may include one or more portions of different flexibility comprising, for example, a more flexible material. Distal end 110 of catheter 108 may have a swivel motion, which allows the distal end 110 to be steerable in all directions. Further, the distal end 110 may be rotatable about a longitudinal axis.

Here, lumens 304A, 304B can be sized to provide a close tolerance fit to the arms 104A, 104B. Alternatively, arms 104A, 104B can be designed to provide a good or a close tolerance fit to lumens 304A, 304B. That sizing provides not only for firmly holding the tool, but it also provides a seal against any ingress of body fluids and materials. In some embodiments, sizing of lumens may be selectively controlled. For example, an expandable member (not shown) may be disposed at the openings of lumens 304A, 304B that may be expanded to create a seal about arms 104A, 104B.

In addition, the outer surface of catheter 108 may include any suitable coating, covering and/or surface features. For example, an outer surface of catheter 108 may include a layer of lubricous material to facilitate insertion of catheter 108 through the elongate member 202 or body lumens. Outer surface of catheter 108 may further comprise surface features, such as ribbing or grooves to facilitate movement in endoscopic or body lumens.

Figure 4:
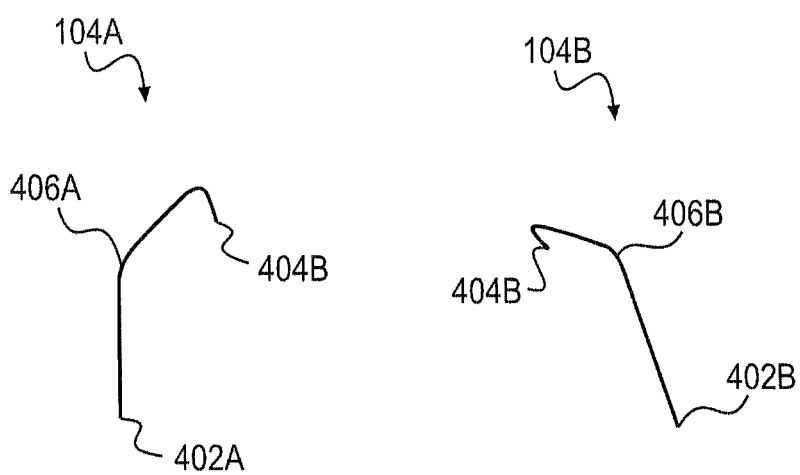
FIGS. 4A and 4B are perspective views of the arms of the exemplary cutting tool shown in FIG. 1.

FIGS. 4A-4B are perspective views of the arms 104A, 104B. These arms have proximal and distal ends 402A, 402B and 404A, 404B, respectively. As shown in FIG. 1, in operation the arms 104A and 104B extend from within the distal end of catheter 108, and they are mounted in the catheter as noted above. Arms 104A, 104B may be made of any suitable material, including, but not limited to, nitinol, ePTFE, fabric, and suitable shape memory or super elastic materials. The chosen material should be compatible with living tissue or a living system, non-toxic or non-injurious, and free from immunological reaction or rejection. Arms 104A, 104B may be pre-formed into the angular shapes described above.

Arms 104A, 104B are configured to transition between compressed and deployed configurations. For example, during the portion of operation which the endoscope is inserted into a patient's bodily lumen or cavity, the catheter 108 is withdrawn into the distal end of the endoscope 102, and in that configuration the arms 104A, 104B are compressed to fit inside catheter 108. Thus, the arms 104A, 104B must possess sufficient resilience to undergo prolonged bending and then recover their preformed angular shape once they are advanced out of the catheter 108. If arms 104A, 104B are only partially extended out of sheath, they may form a partially bended state, which may be desirable for a specific task or anatomy.

In some embodiments, arms 104A, 104B may be selectively expanded to form a desired shape. Angles at which each arm 104A or 1048 diverges from the catheter 108 can be changed, as desired. The super elastic or elastic materials such as nitinol, noted above, are well-suited to this requirement. Super elastic or elastic materials are available to the art in both solid and braided forms, as may be desired for particular applications.

Furthermore, radiopaque or sonoreflective indicia (not shown) may be added to an exterior surface of the arms 104A, 104B to facilitate detecting and tracking the arms' distal tips 111A, 111B for accurate positioning within the patient's body.

In addition, in an embodiment, arms 104A, 104B may be made of discrete sections movably linked to one another. Each section may move relative to the adjacent sections, imparting flexibility to the arms 104A, 104B. Arms 104A, 104B may further comprise variable stiffness along their length influenced, for example, by utilizing materials of different flexibility, or by varying wall thickness and/or cross-sectional geometry of the desired section.

Figure 5:
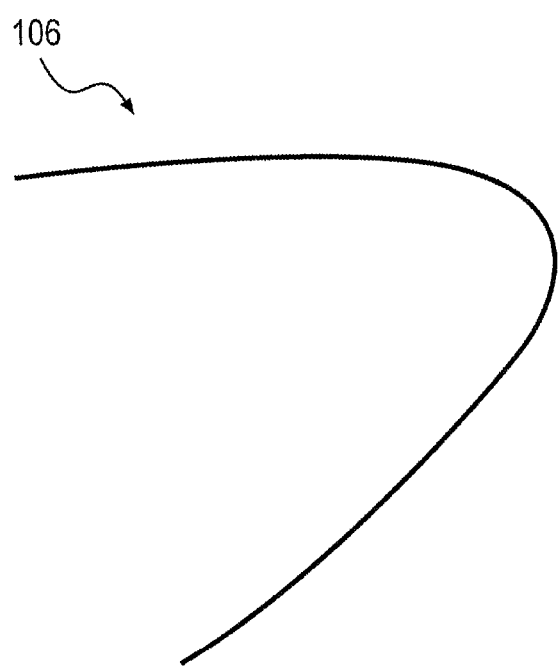
FIG. 5 is a perspective view of a cutting wire of the exemplary cutting tool shown in FIG. 1.

FIG. 5 is a perspective view of the cutting wire 106. In one embodiment, cutting wire 106 may be any suitable wire form capable of cutting tissue. For example, cutting wire 106 may include sharpened outer edges. In some embodiments, cutting wire 106 may have any cross-sectional geometry including, but not limited to, square, flat, rectangular, round, semi-circular, and triangular. Furthermore, the cutting wire 106 cross-sectional geometry may vary along its length. In another embodiment, cutting wire 106 may be configured for electrocauterization procedures; it may conduct electricity. Electrocauterization is the process of destroying tissue using heat generated by passing an electric current through a metal probe or wire. That procedure may be used to stop bleeding from small vessels or for cutting through soft tissue. Here, the cutting wire 106 may be adapted to carry sufficient current to generate the heat required for electrocautery. Furthermore, the wire should be able to withstand repeated heat cycling without developing "hot spots" and breaking down. In some embodiments, cutting wire 106 may include insulation along any portion or portions. Alternatively, cutting wire 106 may have features, such as bumps to deliver energy to focused areas. The cutting wire 106 may be a single strand of wire, formed as solid or braided material. Though the cutting wire and its embodiments have been demonstrated with the electrical energy, it would be evident to persons skilled in the art that other energy sources may be utilized. For example, radio frequency, laser, or ultrasonic. In addition, cutting wire 106 may include features to focus energy delivered. These features may include, e.g., bumps or focal points.

In another embodiment, the wire 106 may be a substantially hollow wire having one or more holes (not shown) disposed on its surface. This arrangement may facilitate additional capabilities, such as irrigation, medication, or lubrication, during the cutting process. The wire may also comprise abrasive coatings or projections, such as barbs, saw, or blades, although such protrusions should be sized to allow movement of the wire through the tool. In some embodiments, cutting wire 106 edge may be sharpened as a blade. Alternatively, cutting wire 106 may include serrations, bumps, or notches. The general characteristics of suitable cutting materials are known in the art, and that knowledge will suffice to select adequate materials for cutting wire 106. In one embodiment, the wire may be made of, e.g., stainless steel.

Cutting wire devices known in the art generally require periodic replacement of the cutting wire. Not only is it often desirable to employ a fresh cutting surface, but the cutting wire can become fouled with remnants of excised tissue. Alternatively, in the case of a cutting wire capable of electrocauterization, the cutting wire may become contaminated with burnt tissue, which may inhibit the cutting procedure. The present disclosure presents a structure that allows rapid and convenient replenishment of the cutting portion of cutting wire 106.

Figure 6:
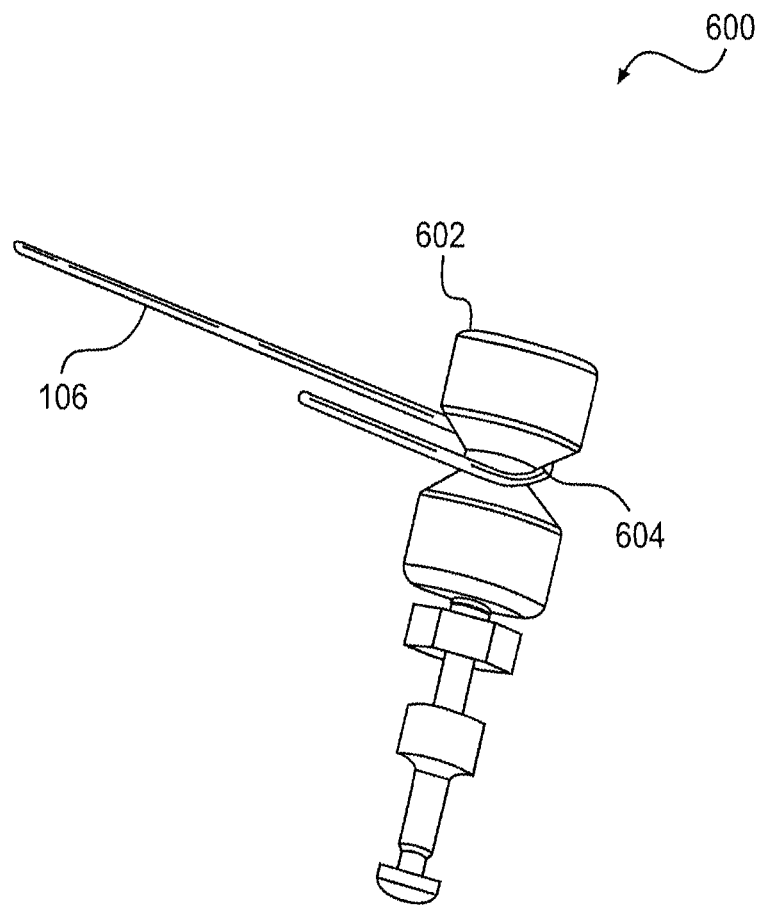
FIG. 6 is a perspective view of a mechanism for advancing or retracting the cutting wire of FIG. 5.

As seen in FIG. 6, cutting wire 106 may be engaged by a rotating means such as pulley 602 or wind-up reel. Pulley 602 may be located at any useful point along catheter 108 or an endoscope, typically at the proximal end. The pulley mechanism 602 may further include a recessed portion 604 adapted to receive one or more wraps of cutting wire 106. For example, the mechanism may include two spools of cutting wire, one fresh, and one used. Mounting hardware can likewise be selected from among the materials and components known in the art for carrying devices such as pulley 602 in a rotatable, stable manner. Similarly, pulley 602 may be fashioned from any of a variety of suitable materials that combine desired characteristics of strength and friction. As should be clear, portions of the pulley 602 may include an electrical insulator material either in composition of the pulley 602 or as a coating. Alternatively, portions of the pulley 602 in contact with the cutting wire 106 may be conductive if it acts as the path for cautery cutting. For example, in FIG. 6, the pulley 602 is connected to a banana plug. The actuation knob may be insulative.

FIG. 6 shows a perspective view of the rotating means to circulate the cutting wire 106. A rotatable element 600 such as a pulley 602 may pull the cutting wire 106 across from one wire-spanning arm 104A towards the other wire-spanning arm 104B. As the cutting wire 106 cuts or cauterizes tissues, tissue remnants, including, e.g., burnt tissue, may adhere to the cutting wire 106 hindering further cutting or cauterization. To prevent this, pulley 602 may be used to circulate the cutting wire 106 such that a fresh portion of cutting wire 106 may be used in subsequent cutting procedures. This eliminates the need to withdraw the cutting tool to change or clean cutting wire 106. Alternatively, a spool of cutting wire 106 may be present at the proximal end of the catheter 108 and/or an endoscope, which may provide a fresh cutting wire 106 for the surgical procedure. In some embodiments, the pulley mechanism 602 may include two spools of cutting wire. For example, a first spool may be used to collect or hold wire already used to cut tissue, and a second spool may hold unused wire. In some embodiments, the lower end of pulley 602 may include a plug for facilitating electrical connection when the cutting wire 106 is a cautery tool. In alternate embodiments, an electrical connector or adaptor may be attached to the proximal end of the catheter 106 and a conductor may connect the adaptor to the pulley 602.

Figure 7:
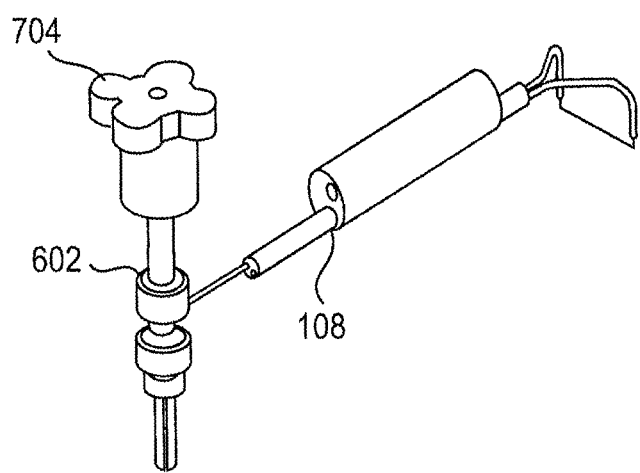
FIG. 7 is an additional view of the mechanism for FIG. 6.

FIG. 7 illustrates the employment of pulley 602 to form a circulating cutting wire 106. As seen, the wire extends from a spool or other suitable source (not shown), through one of the channels 304A, 304B of catheter 108 and into wire passageway in arms 104. Crossing between distal tips of the arms 104A, 104B, the wire enters the opposite wire passageway and returns through catheter 108. At the proximal end of endoscope 102, pulley 602 may be mounted in a convenient location to engage cutting wire 106, which wraps around the pulley one or more times. Endoscope 102 itself has been omitted from this view for clarity. A knob 704 is fixed to pulley 602 in a convenient location for manipulation by an operator. Turning the knob rotates the pulley, drawing cutting wire 106 from the spool, through the device, and on to the pulley. In that manner, a completely new wire section may be exposed for subsequent use. In some embodiments, a second spool of unused wire is not integral with the pulley 602. The second spool may be located at any useful position along the catheter 108, typically at the proximal end. In some embodiments, pulley 602 may include both ends of the cutting wire 106. During operation, rotation of knob 704 both advances a new portion of wire and retracts a used portion of wire at the site of tissue interaction.

Catheter 108 and arms 104A, 104B may be integral; essentially the arms 104A, 104B form the catheter 108 and no separate catheter 108 is needed. In this embodiment, the medical device includes only the arms and their respective lumens.

A number of alternative structures adapted to circulate the cutting wire will be apparent to those in the art. The means for manually rotating the pulley, provided by knob 704, for example, could be replaced by a motor and controller. Or, a monitoring device to determine exactly how much cutting wire 106 is advanced at one time could likewise be added. These and other variations can be made within the scope of the present disclosure.

Figure 8:
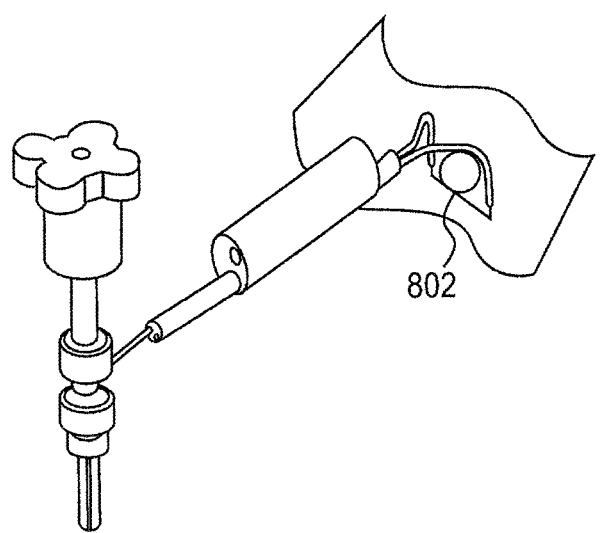
FIG. 8 illustrates an exemplary procedure carried out with the embodiment of FIG. 1.

FIG. 8 shows a perspective view of the system acting on undesired tissue, such as, for example, a lesion 802. Again, endoscope 102 is omitted for clarity. In the depicted scenario, the clinician has navigated endoscope 102 through the patient's body, such as through the GI tract, to the site where tissue removal is required. Here, a lesion 802 is depicted, but those in art understand that the disclosed device can be employed for cutting operations including tissue removal, such as in a polypectomy, or a biopsy, where tissue is excised and then retrieved for analysis. In each the procedure, the distal end of the endoscope 102 is brought into proximity to the lesion 802 and then catheter 108 is distally extended closer to the lesion. Finally, arms 104A, 104B are extended, bringing cutting wire 106 into contact with lesion 802. Cutting wire 106 may be configured to perform a cauterization procedure.

Once contact is made, the cutting process can proceed, employing conventional techniques. After cutting, the clinician may wish to perform additional procedures. For example, there may be multiple polyps or bleeding vessels that may require cauterization. In that event, the operator may advance cutting wire 106 within the arms 104A, 104B by a desired amount using rotating knob 704. Movement of the wire provides a fresh wire, which is not fouled by burned tissue; allowing the clinician to proceed further procedures.

It will be apparent to those in the art that the present disclosure lends itself to a wide variety of embodiments, and to an equally wide variety of applications. A limitation to tissue resection has been the inability to clear the cutting instrument of tissue remnants, a problem addressed here. Thus, it could be reasonably foreseen that embodiments of the present disclosure could be employed in a number of fields, ranging from conventional tissue removal to more involved procedures.

Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. A medical device for cutting tissue, the medical device comprising:
    an elongate tubular member including a proximal end, a distal end, and first and second lumens extending therebetween, wherein a central longitudinal axis of the first lumen is radially offset from a central longitudinal axis of the second lumen;
    a first elongate arm comprising a third lumen and extending through the first lumen;
    a second elongate arm comprising a fourth lumen and extending through the second lumen; and
    a cutting element extending from the third lumen of the first arm to the fourth lumen of the second arm, wherein the cutting element is slidably disposed in the third and fourth lumens.

2. The medical device of claim 1, wherein the device further comprises an introduction sheath.

3. The medical device of claim 1, wherein the cutting element extends from the proximal end of the tubular member to the distal end.

4. The medical device of claim 1, wherein the cutting element comprises a cautery wire.

5. The medical device of claim 1, further comprising a mechanism for circulating the cutting wire between the first and second arms.

6. The medical device of claim 5, wherein the mechanism is configured to circulate the cutting wire such that a first portion disposed between the first and second elongate arms is advanced into one of the lumens of the first and second arms, and a second portion disposed in the other of the lumens of the first and second arms is advanced out of the other of the lumens of the first and second arms.

7. The medical device of claim 5, wherein the mechanism includes a pulley.

8. The medical device of claim 1, wherein the first and second arms are configured to transition between collapsed and expanded configurations.

9. The medical device of claim 1, wherein the arms are movable relative to the elongate tubular member.

10. The medical device of claim 1, wherein the elongate tubular member extends in a first direction and the ends of the arms diverge into separate directions.

11. The medical device of claim 10, at least one of the first and second elongate arms may be configured to transition from a collapsed configuration to an expanded configuration.

12. The medical device of claim 1, wherein a perimeter of the third lumen is completely surrounded by material of the first elongate arm, and wherein a perimeter of the fourth lumen is completely surrounded by material of the second elongate arm.

13. A medical device, comprising:
a plurality of flexible arms extending distally from the distal end of an endoscope, wherein each of the plurality of flexible arms defines a lumen therethrough, and wherein each of the plurality of flexible arms is configured to transition between a first configuration and a second configuration;
a cutting wire extending from one of the plurality of flexible arms to another of the plurality of flexible arms, wherein the cutting wire is slidably disposed within and relative to the lumens of the plurality of flexible arms; and
a mechanism for simultaneously sliding the cutting wire out of one of the plurality of flexible arms and into another of the plurality of flexible arms.

14. The medical device of claim 13, wherein the cutting wire conducts energy.

15. The medical device of claim 13, wherein the first configuration is a collapsed configuration and the second configuration is an expanded configuration.

16. The medical device of claim 13, wherein a portion of the arms are radiopaque.

17. The medical device of claim 13, wherein the wire includes one of protrusions, indentations, and serrations.

18. The medical device of claim 13, wherein the wire includes a blade edge.

19. A method for tissue manipulation, the method comprising:
inserting a medical device within a body lumen, the device including:
an elongate tubular member including a proximal end, a distal end, and first and second lumens extending therebetween, wherein a central longitudinal axis of the first lumen is radially offset from a central longitudinal axis of the second lumen;
a first elongate arm comprising a third lumen and extending through the first lumen;
a second elongate arm comprising a fourth lumen extending through the second lumen, wherein the first and second elongate arms are configured to transition between a collapsed configuration and an expanded configuration; and
a cutting element extending from within the third lumen of the first arm to the fourth lumen of the second arm, wherein the cutting element is slidably disposed in the third and fourth lumens;
advancing the elongate member towards target tissue such that a first portion of the cutting element contacts the target tissue;
resecting the target tissue; and
moving the first portion of the cutting element into one of the third and fourth lumens so that a second portion of the cutting element is in position for tissue contact.

20. The method of claim 19, wherein moving the first portion of the cutting element includes simultaneously circulating the first portion of the cutting element into one of the third and fourth lumens, and the second portion of the cutting element out of the other of the third and fourth lumens.

* * * * *